(12) United States Patent
Röttger et al.

(10) Patent No.: US 6,570,033 B2
(45) Date of Patent: May 27, 2003

(54) BISPHOSPHITE COMPOUNDS AND THEIR METAL COMPLEXES

(75) Inventors: Dirk Röttger, Recklinghausen (DE); Dieter Hess, Marl (DE); Klaus-Diether Wiese, Haltern (DE); Cornelia Borgmann, Recklinghausen (DE); Armin Börner, Rostock (DE); Detlef Selent, Berlin (DE); Reinhard Schmutzler, Wolfenbuettel (DE); Christine Kunze, Vordorf (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/984,263

(22) Filed: Oct. 29, 2001

(65) Prior Publication Data

US 2002/0111487 A1 Aug. 15, 2002

(30) Foreign Application Priority Data

Oct. 27, 2000 (DE) .......................... 100 53 272

(51) Int. Cl.⁷ ................................. C07F 9/08
(52) U.S. Cl. ............................ 558/78; 556/13; 558/77
(58) Field of Search ................... 558/73, 76, 77, 558/78; 556/13, 42, 45, 51, 57; 568/451, 454

(56) References Cited

FOREIGN PATENT DOCUMENTS

DE 196 02 301 7/1996

OTHER PUBLICATIONS

CA:134:131725 abs by Siedentop et al of Zeitschrift fuer Naturforschung B: Chemical Sciences 55(10) pp. 956–960 Oct. 2000.*
CA:113:59752 abs of Tetrahedron by Shadid et al 46(3) pp. 901–912 1990.*
CA:92:199202 abs of Vysokomol. Soedin Ser A by Gur'yanova et al 22(2) pp. 436–442 1980.*
D. Selent, et al., Angew. Chem. Int. Ed. 2001, vol. 40, No. 9, pp. 1696–1698, "New Phosphorus Ligands for the Rhodium–Catalyzed Isomerization/Hydroformylation of Internal Octenes", 2001.
R. Kadyrov, et al., Tetrahedron: Asymmetry, vol. 9, No. 2, pp. 329–340, "New Carbohydrate Bisphosphites as Chiral Ligands", Jan. 30, 1998.
B. Shadid, et al., Tetrahedron, vol. 46, No. 3, pp. 901–912, "The Synthesis of Cytokinin Phosphates", 1990.

* cited by examiner

*Primary Examiner*—Jean F. Vollano
(74) *Attorney, Agent, or Firm*—Oblon, Spivak, McClelland, Maier & Neustadt, P.C.

(57) ABSTRACT

A bisphosphite of the formula I

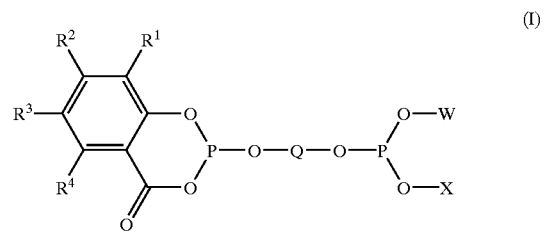

wherein $R^1$, $R^2$, $R^3$ and $R^4$ are each hydrogen, an aliphatic, alicyclic, aliphatic-alicyclic, aromatic, aromatic—aromatic, aliphatic-aromatic hydrocarbon or heterocyclic or aliphatic-heterocyclic group having from 1 to 50 carbon atoms, F, Cl, Br, I, —$CF_3$, —$OR^7$, —$COR^7$, —$CO_2R^7$, —$CO_2M$, —$SR^7$, —$SO_2R^7$, —$SOR^7$, —$SO_3R^7$, —$SO_3M$, —$CO_2NR^7R^8$, $NR^7R^8$, N=$CR^7R^8$, $NH_2$, where $R^1$ to $R^4$ are identical or different and may be covalently linked to one another;

$R^7$ and $R^8$ are each hydrogen, a substituted or unsubstituted, aliphatic or aromatic hydrocarbon radical having from 1 to 25 carbon atoms, and may be identical or different;

M is an alkali metal, alkaline earth metal, ammonium or phosphonium ion;

Q is a substituted or unsubstituted divalent aliphatic, alicyclic, aliphatic-alicyclic, aromatic, aliphatic-aromatic hydrocarbon, heterocyclic or aliphatic-heterocyclic radical having from 1 to 50 carbon atoms where HO-Q-OH is a diol;

W and X are each a substituted or unsubstituted aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms which may be identical or different or covalently linked to one another, provided that when the phosphite oxygens linked to W and X are each linked to an aromatic ring, then they are linked to different aromatic rings, metal complexes thereof, and a method for the hydroformylation of olefins.

22 Claims, No Drawings

BISPHOSPHITE COMPOUNDS AND THEIR METAL COMPLEXES

BACKGROUND OF THE INVENTION

1. Field of the Invention

The present invention relates to bisphosphites and their metal complexes, and the preparation and the use of the bisphosphites as ligands in catalytic reactions.

2. Description of the Background

The reaction between olefin compounds, carbon monoxide and hydrogen in the presence of a catalyst to form aldehyde product having one more carbon atom than the carbon atom content of the starting olefin is known as hydroformylation (the oxo process). The catalysts used in these reactions are frequently compounds of transition metals of Group VIII of the Periodic Table of the Elements, in particular compounds of rhodium and of cobalt. In comparison with catalysis using cobalt compounds, hydroformylation using rhodium compounds generally offers the advantage of higher selectivity and is thus usually more economical. In rhodium-catalyst hydroformylation, use is usually made of complexes comprising rhodium and preferably trivalent phosphorus compounds as ligands. Examples of known ligands are compounds from the classes of the phosphines, phosphites and phosphonites. A good review of the hydroformylation of olefins may be found in B. CORNILS, W. A. HERRMANN, "Applied Homogeneous Catalysis with Organometallic Compounds" Vol. 1&2, VCH, Weinheim, New York, 1996.

Each catalyst system (cobalt or rhodium) has its specific advantages. For this reason, different catalyst systems may be used depending on the starting material and target product, as the following examples show. When rhodium and triphenylphosphine are employed, α-olefins can be hydroformylated at relatively low pressures. An excess of triphenylphosphine is generally used as phosphorus-containing ligand, and a high ligand/rhodium ratio is necessary to increase the selectivity of the reaction to the commercially desired n-aldehyde product.

U.S. Pat. Nos. 4,694,109 and 4,879,416 describe bisphosphine ligands and their use in the hydroformylation of olefins at low synthesis gas pressures. Particularly in the hydroformylation of propane, ligands of this type achieve high activities and high n/i selectivities. WO 95/30680 discloses bidentate phosphine ligands and their use in catalysis, including hydroformylation reactions. Ferrocene-bridged bisphosphines are described as ligands for hydroformylation reactions in, for example, the U.S. Pat. Nos. 4,169,861, 4,201,714 and 4,193,943.

The disadvantage of bidentate phosphine ligands is the relatively high cost of preparing them. It is therefore often not economically viable to use such systems in industrial processes.

Rhodium-monophosphite complexes are suitable catalysts for the hydroformylation of branched olefins having internal double bonds, but the selectivity to terminally hydroformylated compounds is low. EP 0 155 508 discloses the use of bisarylene-substituted monophosphites in the rhodium-catalyst hydroformylation of sterically hindered olefins, e.g. isobutene.

Rhodium-bisphosphite complexes catalyze the hydroformylation of linear olefins having terminal and internal double bonds, forming predominantly terminally hydroformylated products, while branched olefins having internal double bonds are reacted to only a small extent. On coordination to a transition metal center, these phosphites provide catalysts having increased activity, but the operating life of these catalysts systems is unsatisfactory because of, inter alia, the hydrolysis sensitivity of the phosphite ligands. Considerable improvements have been achieved by use of substituted bisaryl diols as starting materials for the phosphite ligands, as described in EP 0 214 622 and EP 0 472 071. According to the literature, the rhodium complexes of these ligands are extremely active hydroformylation catalysts for a-olefins. U.S. Pat. Nos. 4,668,651, 4,748,261 and 4,885,401 describe polyphosphite ligands by means of which c-olefins and also 2-butene can be converted highly selectively to the terminally hydroformylated products. Bidentate ligands of this type have also been used for the hydroformylation of butadiene (U.S. Pat. No. 5,312,996).

Although the bisphosphites mentioned are very good complexing ligands for rhodium hydroformylation catalysts, the need continues to exist for bisphosphites of improved effectiveness.

SUMMARY OF THE INVENTION

Accordingly, one object of the present invention is to provide a bisphosphite ligand for the preparation of olefin hydroformylation catalysts of improved effectiveness.

Briefly, this object and other objects of the present invention as hereinafter will become more readily apparent can be attained by a bisphosphite of the formula I:

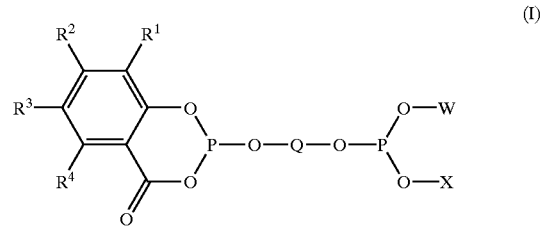

(I)

wherein:

$R^1$, $R^2$, $R^3$ and $R^4$ are each hydrogen, an aliphatic, alicyclic, aliphatic-alicyclic, aromatic, aromatic—aromatic, aliphatic-aromatic hydrocarbon or heterocyclic or aliphatic-heterocyclic radical having from 1 to 50 carbon atoms, F, Cl, Br, I, —$CF_3$, —$OR^7$, —$COR^7$, —$CO_2R^7$, —$CO_2M$, —$SR^7$, —$SOR^7$, —$SO_3R^7$, —$SO_3M$, —$SO_2NR^7R^8$, $NR^7R^8$, N=$CR^7R^8$, $NH_2$, where $R^1$ to $R^4$ are identical or different and may be covalently linked to one another;

$R^7$ and $R^8$ are each hydrogen, a substituted or unsubstituted, aliphatic or aromatic hydrocarbon radical having from 1 to 25 carbon atoms, and may be identical or different;

M is an alkali metal, alkaline earth metal, ammonium or phosphonium ion;

Q is a substituted or unsubstituted divalent aliphatic, alicyclic, aliphatic-alicyclic, aromatic—aromatic, aromatic, aliphatic-aromatic hydrocarbon or heterocyclic or aliphatic-heterocyclic radical having from 1 to 50 carbon atoms; and in open-chain structural elements, one or more methylene groups may be replaced by oxygen and/or sulfur and/or $NR^1$ and/or NH and/or one or more CH groups may be replaced by nitrogen.

W and X are each a substituted or unsubstituted aliphatic, alicyclic, aliphatic-alicyclic, aromatic, aromatic— aromatic, aliphatic-aromatic hydrocarbon, heterocyclic or aliphatic-heterocyclic radical having from 1 to 50 carbon atoms which may be identical or different or covalently linked to one another.

DETAILED DESCRIPTION OF THE PREFERRED EMBODIMENTS

In formula I above, in any given embodiment of the bisphosphite compound, two of the radicals $R^1$ to $R^4$ in the formula I may be benzofused, i.e. $R^1$ and $R^2$, $R^2$ and $R^3$ or $R^3$ and $R^4$ may be linked to one another via an aromatic ring. It is thus possible to prepare three isomers which can be used either separately or together as a ligand system. The bisphosphite of formula I can therefore also be in the forms illustrated by formulae II, III and IV as follows:

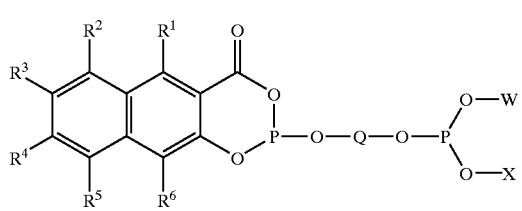
(II)

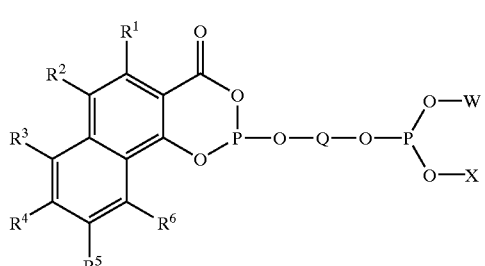
(III)

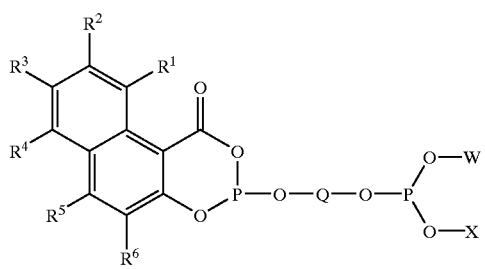
(IV)

The definitions of radicals $R^1$ to $R^6$ correspond to the definitions of $R^1$ to $R^4$ defined for formula I. It is possible for these radicals to be once again covalently linked to one another or benzofused.

Specific embodiments of the bisphosphites of the invention are bisphosphites of the formulae V, VI and VII as follows:

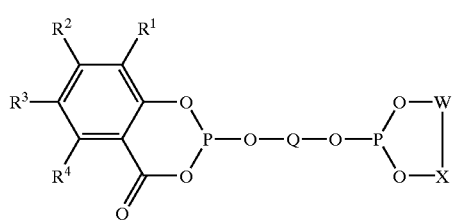
(V)

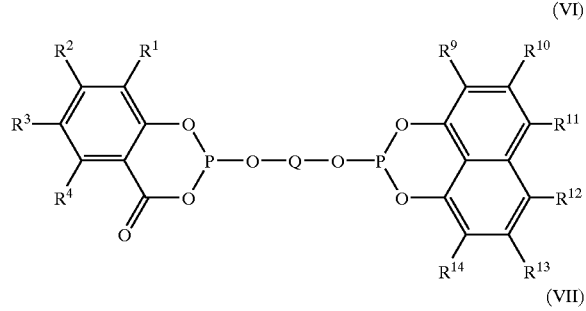
(VI)

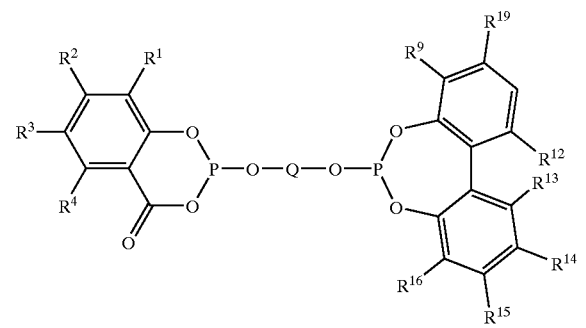
(VII)

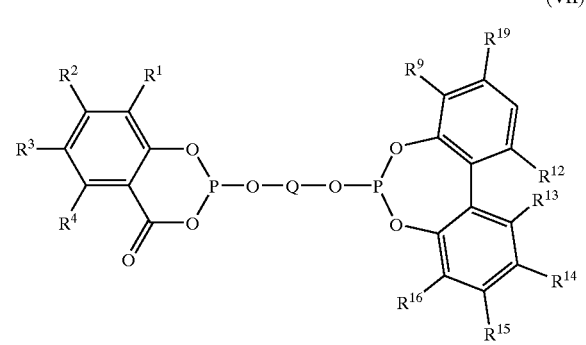

wherein W and X are each substituted or unsubstituted an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, X and W may be identical or different or may be covalently linked to one another and $R^1$, $R^2$, $R^3$, $R^4$, $R^5$, $R^6$, $R^7$ and $R^8$ and Q are as defined above, provided that when the phosphite oxygens linked to W and X are each linked to an aromatic ring then they are not linked to the same aromatic ring.

$R^9$, $R^{10}$, $R^{11}$, $R^{12}$, $R^{13}$, $R^{14}$, $R^{15}$ and $R^{16}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, $-CF_3$, $-OR^{25}$, $-COR^{25}$, $-CO_2R^{25}$, $-CO_2M$, $-SR^{25}$, $-SO_2R^{25}$, $-SOR^{25}$, $-SO_3R^{25}$, $-SO_3M$, $-SO_2NR^{25}R^{26}$, $NR^{25}R^{26}$, $N=CR^{25}R^{26}$, $NH_2$, where $R^9$ to $R^{16}$ are identical or different and may be covalently linked to one another.

M is an alkali metal, alkaline earth metal, ammonium or phosphonium ion.

$R^{25}$ and $R^{26}$ may be identical or different and may each be hydrogen or a substituted or unsubstituted, aliphatic or aromatic hydrocarbon radical having from 1 to 25 carbon atoms.

Examples of Q are bivalent hydrocarbon radicals, which may be aliphatic, alicyclic, aliphatic-alicyclic, aromatic, aromatic—aromatic or aliphatic-aromatic or heterocyclic or aliphatic-heterocyclic bivalent radicals. Any ring system present may in turn be substituted by the abovementioned hydrocarbon radicals. In open-chain structural elements, one or more methylene groups may be replaced by oxygen and/or sulfur and/or $NR^1$ and/or NH and/or one or more CH groups may be replaced by nitrogen.

Q is preferably a bivalent radical containing aromatic groups. Q may be, for example, a phenylene radical, a naphthalene radical, a bivalent bisarylene radical or a bivalent radical of diphenyl ether. Furthermore, Q may have the structure —Ar—Z—Ar—. Here, Ar is a monocyclic or oligocyclic bivalent aromatic radical. Z is either a direct bond or a substituted or unsubstituted methylene group —CR$^{27}$R$^{28}$—, where R$^{27}$ and R$^{28}$ are hydrogen and/or aliphatic and/or aromatic radicals which have from 1 to 25 carbon atoms and may also contain heteroatoms. Furthermore, the radicals R$^{27}$ and R$^{28}$ may be linked to form one or more rings, i.e. be covalently bound.

Among the bisphosphites of the formulae I, II, III, IV, V, VI and VII, particularly preferred are those compounds in which radical Q is a hydrocarbon radical (bisarylene radical) of the formula VIII

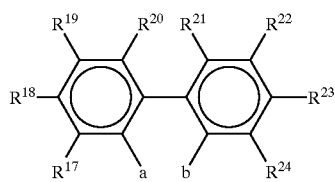

(VIII)

where

- R$^{17}$, R$^{18}$, R$^{19}$, R$^{20}$, R$^{21}$, R$^{22}$, R$^{23}$ and R$^{24}$ are each hydrogen, an aliphatic, alicyclic, aliphatic-alicyclic, heterocyclic, aliphatic-heterocyclic, aromatic—aromatic, aromatic, aliphatic-aromatic hydrocarbon radical having from 1 to 50 carbon atoms, F, Cl, Br, I, —CF$_3$, —OR$^{25}$, —COR$^{25}$, —CO$_2$R$^{25}$, —CO$_2$M, —SR$^{25}$, —SO$_2$R$^{25}$, —SOR$^{25}$, —SO$_3$R$^{25}$, —SO$_3$M, —SO$_2$NR$^{25}$R$^{26}$, NR$^{25}$R$^{26}$, N=CR$^{25}$R$^{26}$, NH$_2$, where R$^{17}$ to R$^{24}$ are identical or different and may be covalently linked to one another;

- R$^{25}$ and R$^{26}$ are each hydrogen, a substituted or unsubstituted, aliphatic or aromatic hydrocarbon radical having from 1 to 25 carbon atoms;

- M is an alkali metal, alkaline earth metal, ammonium or phosphonium ion, where the positions a and b are linkage points of this substituent in the structural element O—Q—O in the compounds of the formulae I to VII.

The present invention also provides bisphosphite-metal complexes comprising a metal of transition Group 4, 5, 6, 7 or 8 of the Periodic Table of the Elements and one or more bisphosphites of the formulae I, II, III, IV, V, VI and VII. The substituents (R$^1$–R$^{26}$, Q, X, W) of these bisphosphites are as defined above.

Representative examples of ligands of the formulae I, II, III, IV, V, VI and VII according to the present invention are presented below, which compounds should not be taken to limit or restrict the scope of the present invention.

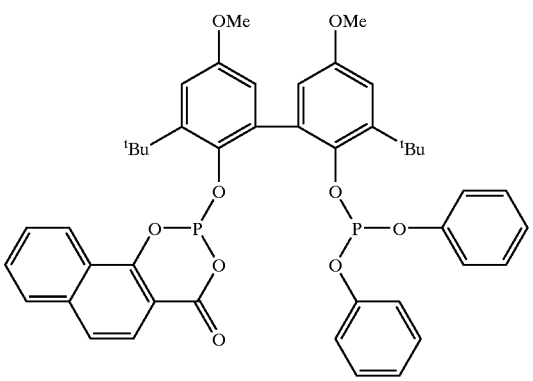

1-a

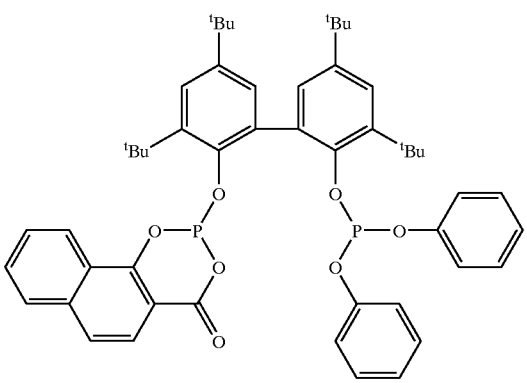

1-b

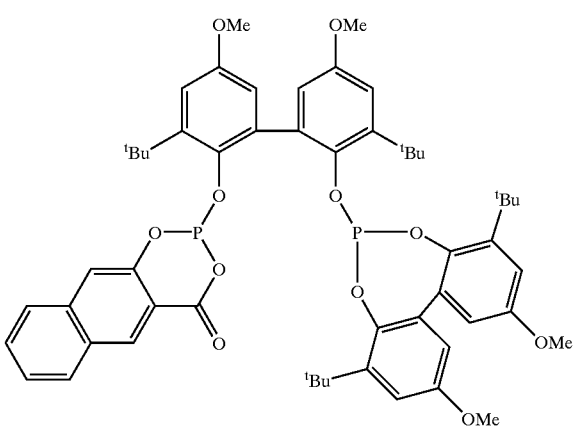

2-a

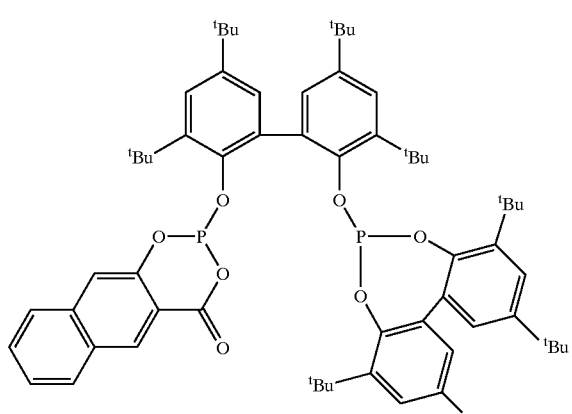

2-b 3-a
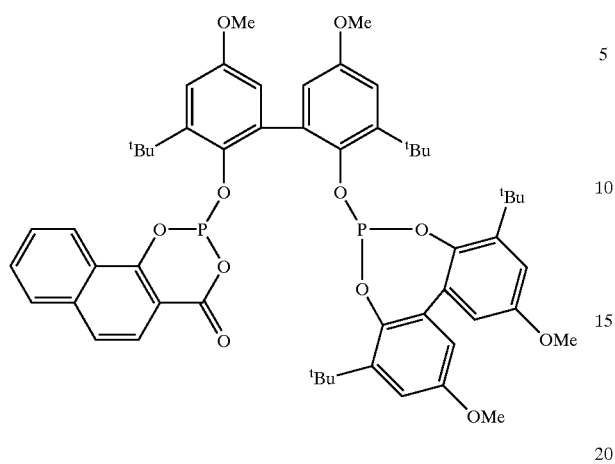
3-b
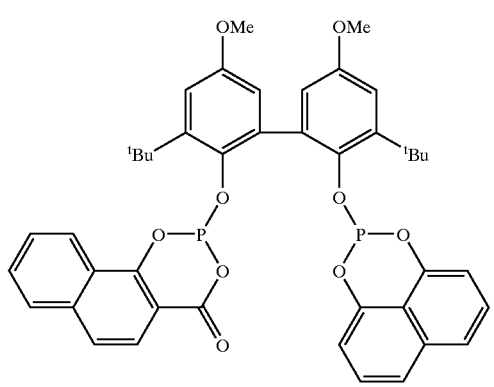
4-a
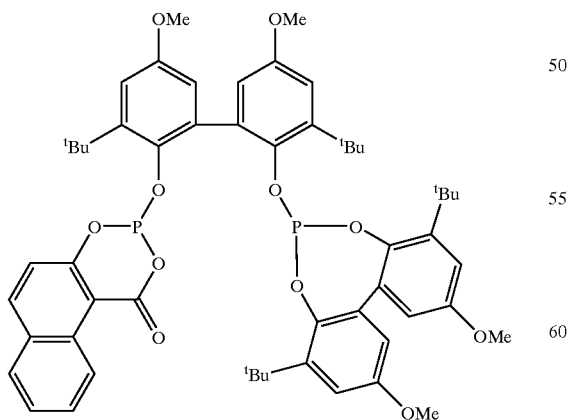
4-b
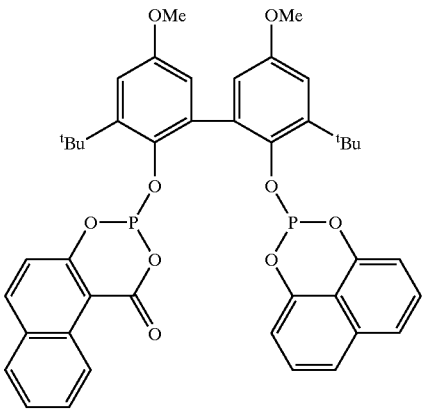
5-a
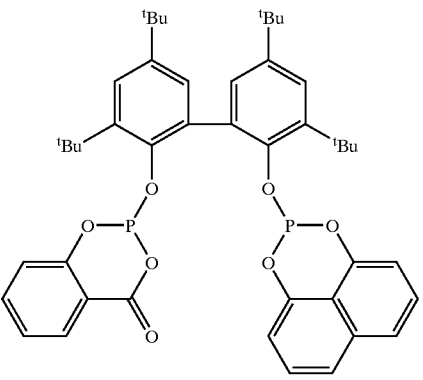
6-a
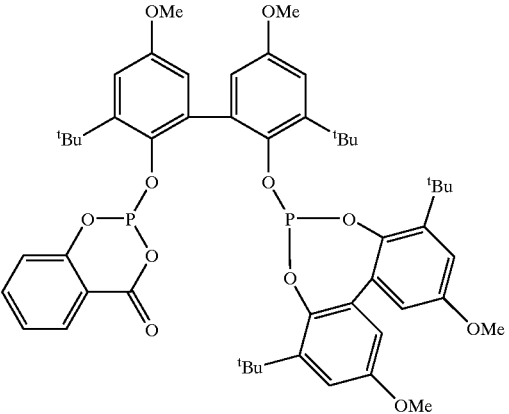

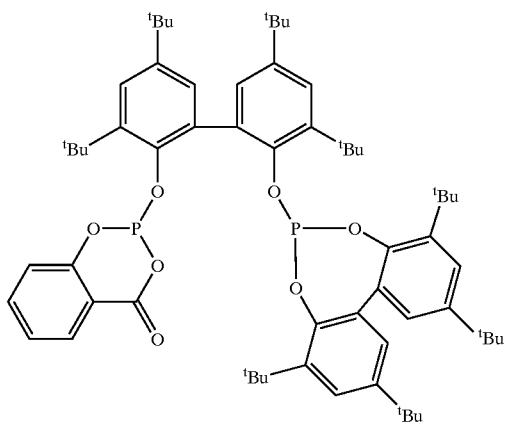
6-b

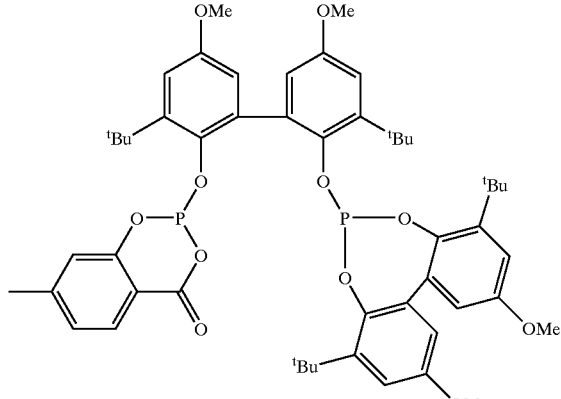
6-e

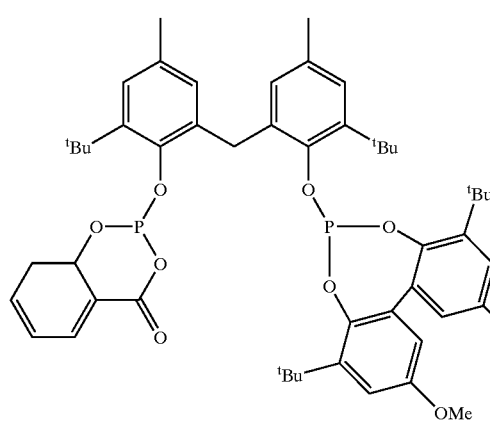
6-c

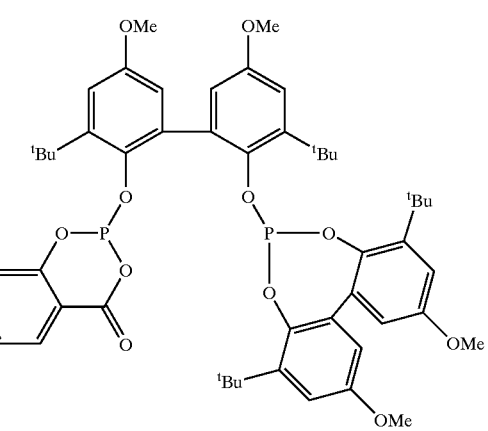
6-f

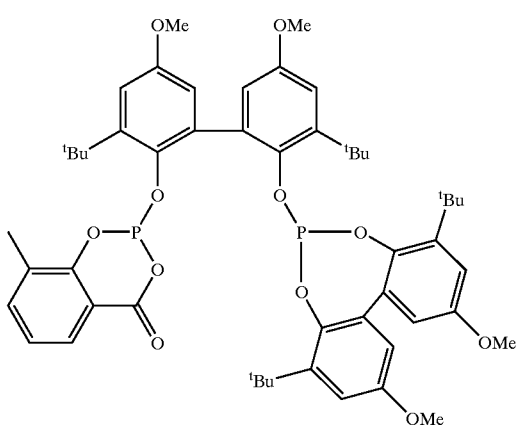
6-d

The bisphosphites of the invention can be prepared by a sequence of reactions of phosphorus halides with alcohols or α-hydroxyarylcarboxylic acids in which the halogen atoms on the phosphorus are replaced by oxygen groups. The fundamental procedure is illustrated by a route to compounds of the formula V:

1) A α-hydroxyarylcarboxylic acid is reacted with a phosphorus trihalide, preferably phosphorus chloride, in the presence of a base to form the intermediate A.

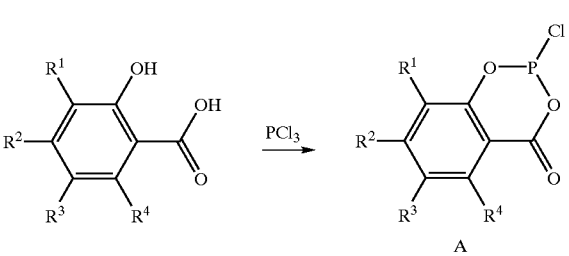

2) A phosphorus trihalide, preferably phosphorus trichloride, is reacted with a diol or two molar equivalents of alcohol to form a monohalophosphite (intermediate B).

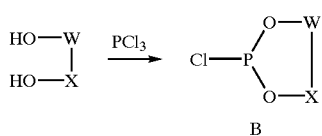

3) A hydroxyl-substituted phosphite (intermediate C) is obtained from the intermediate B by reaction of the intermediate with a diol (HO—Q—OH).

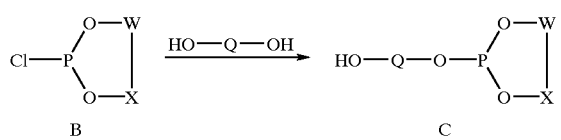

4) The desired bisphosphite is obtained from the reaction of intermediate A with product C.

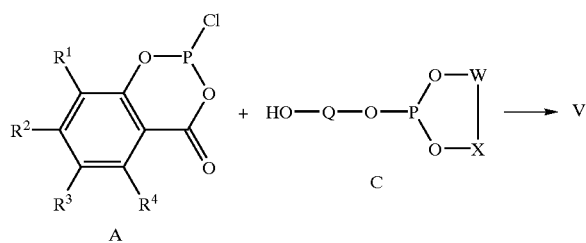

The synthetic route is only one of many, but demonstrates the fundamental procedure. An alternative route is, for example, the reaction of intermediate A with the diol component and subsequent reaction with B to give the desired product.

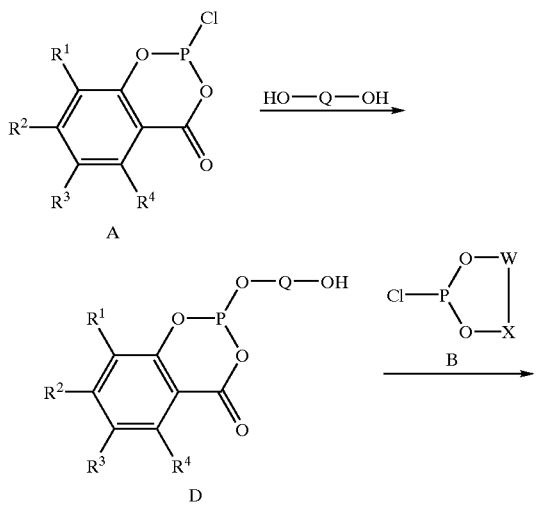

Since the diols used and their downstream products are frequently solid, the reactions are generally conducted in solvents. Suitable solvents are aprotic solvents which react neither with the diols nor with the phosphorus compounds and include tetrahydrofuran, diethyl ether and aromatic hydrocarbons such as toluene.

The reaction of phosphorus halides with alcohols forms hydrogen halide which is sequestered by means of added bases. Examples of bases used for this purpose include tertiary amines such as triethylamine. It is sometimes also useful to convert the alcohols into metal alkoxides, for example, by reaction with sodium hydride or butyllithium, prior to the reaction.

The novel bisphosphites of the formulae I, II, III, IV, V, VI and VII are suitable building blocks for the preparation of complexes with metals of transition Groups 4, 5, 6, 7 and 8 of the Periodic Table of the Elements. These complexes, especially those of metals of transition group 8, can be used as catalysts for carbonylation reactions or hydroformylation reactions, e.g. for the hydroformylation of $C_2$–$C_{25}$-olefins. The ligands have a high hydrolysis stability. Particularly when using rhodium as catalyst metal, high catalytic activities are obtained in hydroformylation reactions. Because of their high molecular weight, the bisphosphites of the invention have a low volatility. They can therefore easily be separated from the less volatile reaction products. They are sufficiently readily soluble in customary organic solvents.

The invention also provides for the use of the bisphosphites or the bisphosphite-metal complexes in processes for the hydroformylation of olefins, preferably those having from 2 to 25 carbon atoms, to form the corresponding aldehydes.

Metals which are preferably used for preparing the catalytically active metal complexes of the bisphosphites of the invention include rhodium, cobalt, platinum and ruthenium. The active catalyst is formed under reaction conditions from the ligand according to the invention and the metal. The ligands of the invention can be added in free form to the reaction mixture. It is also possible to use a transition metal complex comprising one of the abovementioned bisphosphite ligands as precursor for the actual catalytically active complex. The hydroformylation process can be conducted at stoichiometric amounts of metal to bisphosphite or using an excess of free bisphosphite ligands relative to metal containing reactant (e.g. from 1:1 to 200:1).

It is also possible for mixtures of various ligands, both bisphosphites according to the invention, including the isomers of the formulae II to IV, and also other suitable phosphorus-containing ligands, to be present in combination as free ligand components.

Suitable additional ligands present in the reaction mixture include phosphines, phosphites, phosphonites and phosphinites. Specific examples of such ligands are:

Phosphines: triphenylphosphine, tris(p-tolyl)phosphine, tris(m-tolyl)phosphine, tris(o-tolyl)phosphine, tris(p-methoxyphenyl)phosphine, tris(p-dimethylamino-phenyl) phosphine, tricyclohexylphosphine, tricyclopentylphosphine, triethylphosphine, tri-(1-naphthyl) phosphine, tribenzylphosphine, tri-n-butylphosphine, tri-t-butylphosphine.

Phosphites: trimethylphosphite, triethylphosphite, tri-n-propyl phosphite, tri-i-propylphosphite, tri-n-butylphosphite, tri-i-butyl phosphite, tri-t-butylphosphite, tris(2-ethylhexyl)phosphite, triphenylphosphite, tris(2,4-di-t-butylphenyl)phosphite, tris(2-t-butyl-4-methoxyphenyl) phosphite, tris(2-t-butyl-4-methylphenyl)phosphite, tris(p-cresyl) phosphite. In addition, sterically hindered phosphite ligands as described, inter alia, in EP 155 508, U.S. Pat. Nos. 4,668,651; 4,748,261; 4,769,498; 4,774,361; 4,835,299; 4,885,401, 5,059,710; 5,113,022; 5,179,055; 5,260,491; 5,264,616; 5,288,918 and 5,360,938, EP 472 071, EP 518 241 and WO 97/20795 are also suitable ligands.

Phosphonites: methyldiethoxyphosphine, phenyldimethoxyphosphine, phenyldiphenoxyphosphine, 2-phenoxy-2H-dibenz[c,e][1,2]oxaphosphorin and their derivatives in which the hydrogen atoms are wholly or partly replaced by alkyl and/or aryl radicals or halogen atoms, and ligands as are described in WO 98 43935, JP 09-268152 and DE 198 10 794 and in the German patent applications DE 199 54 721 and DE 199 54 510.

Customary phosphinite ligands are described, inter alia, in U.S. Pat. No. 5,710,344, WO 95 06627, U.S. Pat. No. 5,360,938 or JP 07082281. Examples include diphenyl (phenoxy)phosphine and its derivatives in which the hydrogen atoms are wholly or partly replaced by alkyl and/or aryl radicals or halogen atoms, diphenyl(methoxy)phosphine and diphenyl(ethoxy)phosphine. In general, from 1 to 500 mol, preferably from 1 to 200 mol, more preferably from 3 to 50 mol, of the ligand of the invention are used per mole of Group VIII transition metal. Fresh ligand can be added to the reaction at any point in time in order to keep the concentration of free ligand constant. The catalytic transition metal-bisphosphite complexes of the invention can be synthesized before use. However, the catalytically active complexes are generally formed in situ in the reaction medium from a catalyst precursor and the present bisphosphite ligand.

Precursors of the present catalyst include salts and complexes of transition metals. Suitable examples include rhodium carbonyls, rhodium nitrate, rhodium chloride, $Rh(CO)_2(acac)$ (acac=acetylacetonate), rhodium acetate, rhodium octanoate and rhodium nonanoate.

The concentration of the metal in the reaction mixture is in the range from 1 ppm to 1000 ppm, preferably in the range from 5 ppm to 300 ppm.

The hydroformylation reactions conducted using the bisphosphites of the invention or the corresponding metal complexes can be conducted by known methods as described, for example, in J. FALBE, "New Syntheses with Carbon Monoxide", Springer Verlag, Berlin, Heidelberg, New York, page 95 ff., (1980).

The reaction temperatures for a hydroformylation process using the bisphosphites of the invention or bisphosphite metal complexes as catalyst are in the range from 40° C. to 180° C., preferably from 75° C. to 140° C. The pressure under which the hydroformylation occurs ranges from 1–300 bar of synthesis gas, preferably 15–64 bar. The molar ratio of hydrogen to carbon monoxide ($H_2/CO$) in the synthesis gas ranges from 10/1 to 1/10, preferably from 1/1 to 2/1.

The catalyst or ligand is homogeneously dissolved in the hydroformylation mixture comprising starting material (olefins) and products (aldehydes, alcohols, high boilers formed in the process). It is possible, if desired, to use an additional solvent.

The starting materials for the hydroformylation are monoolefins or mixtures of monoolefins having from 2 to 25 carbon atoms and a terminal or internal C—C double bond. The olefins can be linear, branched or cyclic and may also have a plurality of olefinically unsaturated groups. Suitable examples include propene, 1-butene, cis-2-butene, trans-2-butene, isobutene, butadiene, mixtures of $C_4$-olefins, 1- or 2-pentene, 2-methyl-1-butene, 2-methyl-2-butene, 3-methyl-1-butene, 1-, 2- or 3-hexene, the $C_6$-olefin mixtures formed in the dimerization of propene (dipropene), 1-heptene, heptenes, 2- or 3-methyl-1-hexene, 1-octene, octenes, 2-methylheptenes, 3-methylheptenes, 5-methyl-2-heptene, 6-methyl-2-heptene, 2-ethyl-1-hexene, the isomeric $C_8$-olefin mixtures formed in the dimerization of butenes (dibutene), 1-nonene, nonenes, 2- or 3-methyloctenes, the $C_9$-olefin mixtures formed in the trimerization of propene (tripropene), decenes, 2-ethyl-1-octene, dodecenes, the $C_{12}$-olefin mixture formed in the tetramerization of propene or the trimerization of butenes (tetrapropene or tributene), tetradecene, hexadecenes, the $C_{16}$-olefin mixtures formed in the tetramerization of butenes (tetrabutene) and also olefin mixtures prepared by co-oligomerization of olefins having different numbers of carbon atoms preferably from 2 to 4), if desired after fractional distillation to separate them into fractions having the same number of carbon atoms or a similar number of carbon atoms. It is likewise possible to use olefins or olefin mixtures produced by Fischer-Tropsch synthesis, and also olefins which are obtained by oligomerization of ethene or can be produced via methathesis reactions or telomerization reactions.

Preferred starting materials include propene, 1-butene, 2-butene, 1-hexene, 1-octene, dimers and trimers of butene (dibutene, di-n-butene, diisobutene, tributene) and α-olefins in general.

The hydroformylation reaction can be conducted continuously or batchwise. Examples of industrial apparatuses are stirred vessels, bubble columns, jet reactors, tube reactors and loop reactors, which may be cascaded and/or provided with internals.

The reaction can be conducted in a single step or in a plurality of steps. The aldehyde compounds formed and the catalyst can be separated by a conventional method such as fractionation. This can, for example, be carried out industrially by means of a distillation, by means of a falling film evaporator or by means of a thin film evaporator. This is particularly applicable when the catalyst is separated as a solution in a high-boiling solvent from the lower-boiling product. The catalyst solution which has been separated can be used for further hydroformylation. When using lower olefins, e.g. propene, butene, pentene, it is also possible for the products to be discharged from the reactor in gaseous form.

Having generally described this invention, a further understanding can be obtained by reference to certain specific examples which are provided herein for purposes of illustration only and are not intended to be limiting unless otherwise specified.

EXAMPLES

All preparations were conducted under protective gas using standard Schlenk techniques. The solvents were dried over suitable desiccants before use.

2-Chloro-1,3-dioxa-2-phosphaanthracen-4-one employed in the synthesis of bisphosphite compounds was synthesized by the method described in the literature at (BE 667036, Farbwerke Hoechst AG, 1966; Chem. Abstr. 65 (1966) 13741d). 3-Chloro-2,4-dioxa-3-phosphaphenanthren-1-one was obtained in an analogous way. 2-Chloro-2,3-dioxa-2-phosphanaphthalen-4-one (van Boom's Reagenz) is commercially available.

Example 1
Synthesis of the Precursors C-1 and C-2

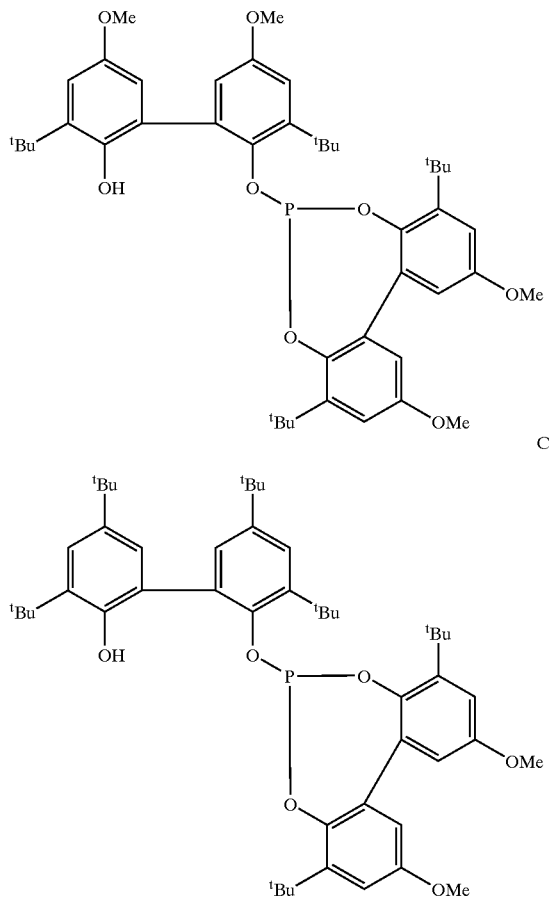

Precursor C-1

A solution of 0.93 g of $PCl_3$ (6.75 mmol) in 10 ml of THF was added dropwise at 0° C. to a solution of 2.42 g of 2,2'-bis(6-tert-butyl-1-hydroxy-4-methoxyphenyl) (6.75 mmol) and 1.6 mol of pyridine in 22 ml of THF. After stirring at 25° C. for 4 hours, the solvent is removed under reduced pressure. Addition of 40 ml of diethyl ether, filtration and evaporation under reduced pressure gives 2.8 g (98%) of spectroscopically pure chlorophosphorous ester of 2,2'-bis(6-tert-butyl-1-hydroxy-4-methoxyphenyl): $^{31}$P-NMR $(CD_2Cl_2)$ δ 172.7 ppm. 2.8 g of this chloroester (6.62 mmol) in 20 ml of THF is added at room temperature to a monolithium phenoxide solution obtained at −20° C. from 2.37 g of 2,2'-bis(6-tert-butyl-1-hydroxy-4-methoxyphenyl) (6.62 mmol) in 30 ml of THF and 20.7 ml of a 0.32 M hexane solution of n-butyllithium (6.62 mmol). After 24 hours, the mixture is evaporated under reduced pressure. Addition of 40 ml of methylene chloride, filtration and removal of the solvent under reduced pressure give 4.6 g (93%) of highly viscous product.

Analysis (calc. for $C_{44}H_{57}O_8P$=744.9 g/mol) C, 70.35 (70.95); H, 7.86 (7.71). $^{31}$P-NMR $(CD_2Cl_2)$ δ 140.7 ppm. $^1$H-NMR $(CD_2Cl_2)$ δ 1.43 (s, 9H); 1.56 (s, 9H); 1.63 (s, 9H); 1.67 (s, 9H); 4.01 (s, 3H); 4.03 (s, 6H); 4.05 (s, 3H); 5.42 (s, 1H); 6.7 . . . 7.3 (m, 8H) ppm. FAB MS: m/e 745 (37%), M⁺); 387 (100%, M⁺-2,2'-bis(6-tert-butyl-1-hydroxy-4-methoxyphenyl). IR ($CHCl_3$, 0.1 mm $CaF_2$), ν(OH)=3549 cm$^{-1}$.

Precursor C-2

The synthesis is carried out in a manner analogous to the preparation of C-1. The chlorophosphite diester is obtained in a virtually quantitative yield (98.4%, $^{31}$P NMR, $CD_2Cl_2$ δ 172.0). For the second step of the reaction sequence, this chlorophosphite diester (10.7 g, 22.5 mmol) is reacted with the product from 1.6 M butyllithium solution in hexane (14.1 ml) and the corresponding dihydroxybiphenyl compound. After removal of the solvent, the residue is extracted a number of times with hot hexane. The product crystallizes from the combined hexane fractions and is isolated and dried under reduced pressure. Yield: 76.4%

Analysis (calc. for $C_{56}H_{81}O_4P$=849.23 g/mol) C, 78.78 (79.20); H, 9.95 (9.61). $^{31}$P-NMR $(CD_2Cl_2)$ δ 142.3 ppm. $^1$H-NMR $(CD_2Cl_2)$ δ 0.98 (s, 9H); 1.15 (s, 9H); 1.21 (s, 9H); 1.22 (s, 9H); 1.23 (s, 9H); 1.24 (s, 9H); 1.30 (s, 9H); 1.36 (s, 9H); 5.35 (s, 1H); 6.99 (d, 1H); 7.01 (d, 1H); 7.05 (d, 1H); 7.06 (d, 1H); 7.26 (d, 2H); 7.32 (d, 1H); 7.36 (d, 1H) ppm.

Example 2
Synthesis of Ligand 2-a

A 9.5 ml amount of a 0.32M solution of n-butyllithium (3.04 mmol) is added dropwise at −20° C. to a solution of 2.27 g of C-1 (3.04 mmol) in 24 ml of THF while stirring. After warming to room temperature, the mixture is firstly stirred for another 30 minutes and the resulting mixture is then added to 22 ml of a 0.138 M solution of 2-chloro-1,3-dioxa-2-phosphaanthracen-4-one (3.04 mmol) in THF. The reaction mixture is stirred at 25° C. for 4 hours, the solvent is removed under reduced pressure and the syrup-like residue is stirred for 2 hours with 60 ml of hexane. The mixture is filtered, and the filter cake is washed with 2×7 ml of hexane and extracted by back distillation of hexane from the filtrate. Storage of the mother liquor for 3 days at 5° C. gives 0.828 g of pure solid. Additional extraction of the filter cake from the hexane extraction with 35 ml of boiling diethyl ether gives, after reduction of the volume of the filtrate to 50% and storage at 5° C., 0.6 g of product. Total yield: 1.428 g=49%. Analysis (calc. for $C_{55}H_{62}O_{11}P_2$=961.03 g/mol) C, 68.69 (68.74); H, 6.73 (6.50); P, 6.41 (6.45)%.$^{31}$P-NMR $(CD_2Cl_2)$: δ 118.1; 119.1; 139.0; 140.2. $^1$H-NMR $(CD_2Cl_2)$: δ 1.15 . . . 1.44 (36H); 3.81 . . . 3.93 (12H); 6.57 . . . 8.71 (14H). FAB-MS: m/e 961 (30%, M⁺); 745 (31%); 727 (97%); 387 (100%).

Example 3
Synthesis of Ligand 3-a

The P—Cl compound used is 3-chloro-2,4-dioxa-3-phosphaphenanthren-1-one. The synthesis is performed starting from 2.31 g of C-1 (3.10 mmol) up to the extraction of the filter cake with backdistilled hexane from the filtrate in a manner analogous to the preparation of 2-a. Subsequent storage of this solution at 5° C. initially gives 0.90 g, after reduction of the volume to half, a further 1.36 g, of product; total yield: 2.26 g=75%. Analysis (calc. for $C_{55}H_{62}O_{11}P_2$= 961.03 g/mol) C, 69.42 (68.74); H, 7.16 (6.50); P, 5.98 (6.45)%.$^{31}$P-NMR $(CD_2Cl_2)$: δ 120.3; 121.1; 139.7; 140.7. $^1$H-NMR $(CD_2Cl_2)$: 0.87 . . . 1.40 (36H); 3.75 . . . 3.88 (12H); 6.63 . . . 8.17 (14H); Cl-MS: m/e 962 (31%, M-H⁺); 745 (100%); 405 (90%); 387 (80%).

Example 4
Synthesis of Ligand 6-a

The P—Cl compound is 2-chloro-1,3-dioxa-2-phosphanaphthalen-4-one. The synthesis is conducted starting from 6.86 g of C-1 up to the extraction of the filter cake in a manner analogous to the preparation of 2-a. The extraction is conducted using hot hexane and using diethyl ether. Reduction of the amount of solvent to one third and subsequent storage of this solution at −20° C. gives the product in a yield of 54%. $^{31}$P-NMR (CD$_2$Cl$_2$): 119.2 (m); δ 119.8 (m); 139.5 (m); 140.1 (m); $^1$H-NMR (CD$_2$Cl$_2$): 1.02 . . . 1.26 (36H); 3.67 . . . 3.74 (12H); 6.43 . . . 7.99 (12H). FAB-MS: m/e 911 (100%, M$^+$), 744 (18%), 387 (13%).

Example 5

Synthesis of Ligand 6-b

The P—Cl compound used is 2-chloro-1,3-dioxa-2-phosphanaphthalen-4-one. The synthesis is conducted starting from 4.93 g of C-2 in a manner analogous to the synthesis of compound 2-a. Total yield: 50.4%. Analysis (calc. for C$_{63}$H$_{84}$O$_7$P$_2$=1015.30 g/mol) C, 74.86 (74.53); H, 8.43 (8.34). $^{31}$P-NMR (CD$_2$Cl$_2$): δ 118.5, 119.7, 142.0, 142.8; $^1$H-NMR (CD$_2$Cl$_2$): 0.90 . . . 1.36 (72H); 6.74 . . . 7.90 (12H); FAB-MS: m/e 1015 (7%, M+), 832 (100%), 439 (70%).

Example 6

Synthesis of Ligand 2-b

The P—Cl compound used is 2-chloro-1,3-dioxa-2-phosphaanthracen-4-one. The synthesis is conducted starting from 5.07 g of C-2 in a manner analogous to the preparation of 2-a. Yield: 73%. Analysis (calc. for C$_{67}$H$_{86}$O$_7$P$_2$=1065.36 g/mol) C, 75.24 (75.54); H, 8.16 (8.14). $^{31}$P-NMR (CD$_2$Cl$_2$): δ 117.8, 118.9, 142.1, 142.9; ratio of the diastereomers=1.3:1. $^1$H-NMR (CD$_2$Cl$_2$): 0.99 . . . 1.35 (72H); 6.95 . . . 8.55 (14H). FAB-MS: m/e 1064 (18%, M-H). 831 (100%), 439 (78%).

Examples 7 and 8

Hydroformylation of 1-Octene

The experiments were conducted in a 200 ml stainless steel autoclave from Buddeberg, Mannheim, which was fitted with a sparging stirrer, pressure pipette and pressure regulator, was located in an oil bath thermostat and had been charged under protective gas. To minimize the influence of moisture and oxygen, the toluene used as solvent was dried by means of sodium cetyl and distilled under argon. The 1-octene used as substrate was refluxed over sodium for a number of hours and distilled under argon.

The autoclave was charged with 27 ml of toluene in which 5.456 mg=0.0176 mmol of [acacRh(COD)] and 0.088 mmol of the respective ligand had been dissolved. The molar ratio of Rh/P was thus 1:10. 24 ml=about 16.8 g (149.3 mmol) of 1-octene were placed in the pressure pipette over the reactor. The ratio of Rh/1-octene was thus about 1:8500. Reactor and pressure pipette were pressurized via a bypass in parallel to the pressure regulation section with 33 bar of CO/H$_2$ (1:1; synthesis gas) at a set pressure of 50 bar and with thirteen bar of CO/H$_2$ at a set pressure of 20 bar, and the contents of the reactor were heated to 80 or 100° C. while stirring magnetically by means of the sparging stirrer at 1500 min$^{-1}$. After reaching the set temperature, the pressure was increased to 47 bar (17 bar) and the olefin mixture was injected from the pressure pipette into the reactor using a pressure of 55 bar (25 bar). An initial reaction pressure of 49.6 bar (19.2 bar) was established. After immediately regulating the pressure manually to 50 bar (20 bar), the bypass was closed and the pressure was kept constant over the entire reaction time by means of the pressure regulator. The experiment was stopped by forcible cooling after the predetermined reaction time had expired. The reaction solution was removed under protective gas and analyzed by gas chromatography.

The following table reports the results obtained using the individual ligands.

| Example | Ligand | Temp. [° C.] | p [bar] | t [h] | Yield [%] | Proportion of nonanal [%] |
|---|---|---|---|---|---|---|
| 7 | 2-a | 100 | 20 | 3 | 81 | 79.0 |
| 8 | 3-a | 100 | 20 | 3 | 79 | 83.8 |

Examples 9–19

Hydroformylation of a Mixture of 1-Octene, 2-Octene, 3-Octene and 4-Octene

The experiments were conducted in a 200 ml stainless steel autoclave from Buddeberg, Mannheim, which was fitted with a sparging stirrer, pressure pipette and pressure regulator and located in an oil bath thermostat. The reactant was charged under protective gas. To minimize the influence of moisture and oxygen, the toluene used as solvent was dried by means of sodium cetyl and distilled under argon. The octene isomer mixture used as substrate was refluxed over sodium for a number of hours and distilled under argon. Composition: 1-octene, 3.3%; cis+trans-2-octene, 48.5%; cis+trans-3-octene, 29.2%; cis+trans-4-octene, 16.4%; branched C$_8$-olefins, 2.6%.

The autoclave was charged with 41 ml of toluene in which 18.75 mg=0.0604 mmol of [acacRh(COD)], the respective bidentate ligand and, if required, the coligand depicted below had been dissolved. The ratio of Rh/bidentate ligand (ligand)/ether phosphonite (co-ligand) is shown in the table. 15 ml=10.62 g (94.63 mmol) of octenes were placed in the pressure pipette over the reactor. The ratio of Rh/octenes was thus about 1:1570. Reactor and pressure pipette were pressurized via a bypass in parallel to the pressure regulation section with 13 bar of CO/H$_2$ (1:1; synthesis gas) and the contents of the reactor were heated to 130° C. while stirring magnetically by means of the sparging stirrer at 1500 min$^{-1}$. After reaching the set temperature, the pressure was increased to 17 bar and the olefin mixture was injected from the pressure pipette into the reactor using a pressure of 25 bar. An initial reaction pressure of 19.2 bar was established. After immediately regulating the pressure manually to 20 bar, the bypass was closed and the pressure was kept constant over the entire reaction time by means of the pressure regulator. The experiment was stopped by forcible cooling after three hours. The reaction solution was taken out under protective gas and analyzed by gas chromatography.

The co-ligand used was:

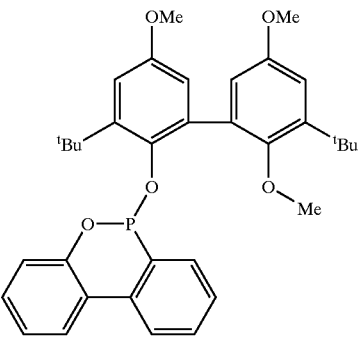

CL-1

The following table reports the results obtained using the individual ligands.

| Example | Ligand/-coligand | T [° C.] | Rh/Lig/CoLig/olefin [mol/mol/mol/mol] | t [h] | Yield [%] | Proportion of nonanal [%] |
|---|---|---|---|---|---|---|
| 9 | 2-a | 130 | 1/5/0/1570 | 3 | 95 | 64.2 |
| 10 | 2-b | 130 | 1/5/0/1570 | 3 | 93 | 67.9 |
| 11 | 3-a | 130 | 1/5/0/1570 | 3 | 96 | 69.0 |
| 12 | 6-a | 130 | 1/5/0/1570 | 3 | 94 | 63.9 |
| 13 | 6-b | 130 | 1/5/0/1570 | 3 | 95 | 67.3 |
| 14 | 2-a/CL-1 | 130 | 1/2.5/5/1570 | 3 | 92 | 63.5 |
| 15 | 3-a/CL-1 | 130 | 1/2.5/5/1570 | 3 | 93 | 67.8 |
| 16 | 6-a/CL-1 | 130 | 1/2.5/5/1570 | 6 | 98 | 63.0 |
| 17# | 3-a | 130 | 1/5/0/15700 | 6 | 74 | 69.5 |
| 18# | 6-a | 130 | 1/5/0/15700 | 6 | 83 | 64.1 |
| 19# | 6-b | 130 | 1/5/0/15700 | 6 | 66 | 69.0 |

0.00604 mmol of [acacRh(COD)], correspondingly less ligand

Examples 20–25

Hydroformylation of Technical-Grade Di-N-Butene

The experiments were conducted by a method analogous to Examples 9–19 using 15 ml=10.70 g (95.34 mmol) of a mixture of isomeric octenes (double bond isomers and skeletal isomers) obtained by dimerization of n-butenes. The following Table reports both results obtained using pure bidentate ligands and results obtained using a mixture of bidentate ligand/co-ligand CL-1.

| Example | Ligand/-coligand | T [° C.] | Rh/Lig/CoLig/olefin [mol/mol/mol/mol] | t [h] | Yield [%] | Proportion of nonanal [%] |
|---|---|---|---|---|---|---|
| 20 | 2-a | 130 | 1/5/0/1578 | 6 | 59 | 63.2 |
| 21 | 2-a/CL-1 | 130 | 1/2.5/5/1578 | 6 | 57 | 63.0 |
| 22 | 3-a | 130 | 1/5/0/1578 | 6 | 56 | 65.7 |
| 23 | 3-a/CL-1 | 130 | 1/2.5/5/1578 | 6 | 60 | 65.4 |
| 24 | 6-a | 130 | 1/5/0/1578 | 6 | 56 | 63.1 |
| 25 | 6-a/CL-1 | 130 | 1/2.5/5/1578 | 6 | 58 | 62.3 |

The disclosure of German priority Application No. 100 53 272.1 filed Oct. 27, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A bisphosphite of formula I

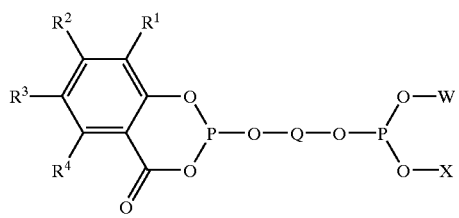

(I)

wherein $R^1$, $R^2$, $R^3$ and $R^4$ are each hydrogen, an aliphatic, alicyclic, aliphatic-alicyclic, aromatic, aromatic—aromatic, aliphatic-aromatic hydrocarbon, heterocyclic or aliphatic-heterocyclic group having from 1 to 50 carbon atoms, F, Cl, Br, I, —$CF_3$, —$OR^7$, —$COR^7$, —$CO_2R^7$, —$CO_2M$, —$SR^7$, —$SO_2R^7$, —$SOR^7$, —$SO_3R^7$, —$SO_3M$, —$SO_2NR^7R^8$, $NR^7R^8$, $N=CR^7R^8$, $NH_2$, where $R^1$ to $R^4$ are identical or different and may be covalently linked to one another;

$R^7$ and $R^8$ are each hydrogen, a substituted or unsubstituted, aliphatic or aromatic hydrocarbon or heterocyclic or aliphatic heterocyclic radical having from 1 to 25 carbon atoms, and may be identical or different;

M is an alkali metal, alkaline earth metal, ammonium or phosphonium ion;

Q is a substituted or unsubstituted divalent aliphatic, alicyclic, aliphatic-alicyclic, aromatic, or aliphatic-aromatic hydrocarbon radical having from 1 to 50 carbon atoms, and in open-chain structural elements, one or more methylene groups may be replaced by oxygen and/or sulfur and/or $NR^1$ and/or NH and/or one or more CH groups may be replaced by nitrogen, W and X are each a substituted or unsubstituted aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms which may be identical or different or covalently linked to one another, where the substituents are selected from the group consisting of an aliphatic, alicyclic, aliphatic-alicyclic, aromatic, aromatic—aromatic, aliphatic-aromatic hydrocarbon, heterocyclic or aliphatic-heterocyclic radical having 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $N=CR^{25}R^{26}$, $NH_2$, where $R^9$ to $R^{14}$ are identical or different and may be covalently linked to one another, provided that when the phosphite oxygens linked to W and X are each linked to an aromatic ring then they are not linked to the same aromatic ring.

2. A bisphosphite as claimed in claim 1, wherein W and X are each an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms which are covalently linked as shown in formula V

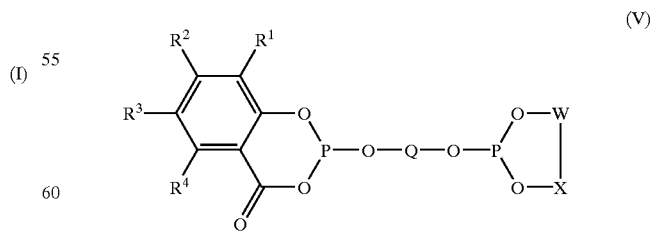

(V)

3. A bisphosphite as claimed in claim 1, wherein W and X are substituted or unsubstituted aromatic hydrocarbon radicals having from 1 to 50 carbon atoms which are covalently linked as shown in formula VI

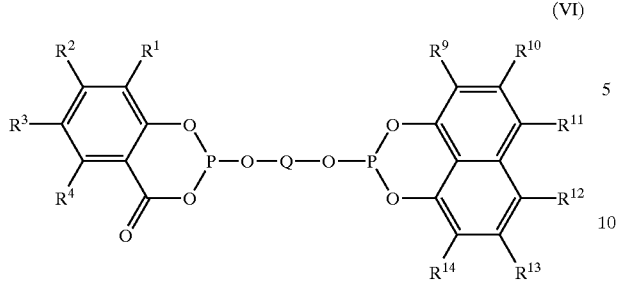

(VI)

wherein $R^9$, $R^{10}$, $R^{11}$, $R^{12}$, $R^{13}$, and $R^{14}$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N{=}CR^{25}R^{26}$, $NH_2$, where $R^9$ to $R^{14}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

4. A bisphosphite as claimed in claim 1, wherein W and X are substituted or unsubstituted aromatic hydrocarbon radicals having from 1 to 50 carbon atoms which are covalently linked as shown in formula VII

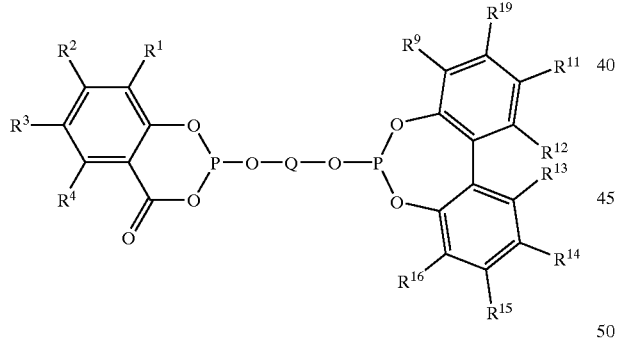

(VII)

where $R^9$, $R^{10}$, $R^{11}$, $R^{12}$, $R^{13}$, $R^{14}$, $R^{15}$ and $R^{16}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N{=}CR^{25}R^{26}$, $NH_2$, where $R^9$ to $R^{16}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

5. A bisphosphite of formula II, III, or IV

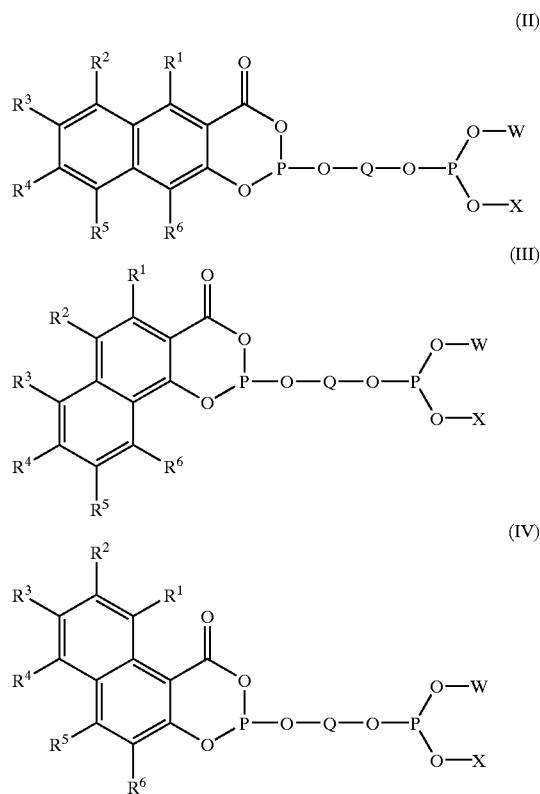

wherein $R^1$, $R^2$, $R^3$, $R^4$, $R^5$ and $R^6$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^7$, —$COR^7$, —$CO_2R^7$, —$CO_2M$, —$SR^7$, —$SO_2R^7$, —$SOR^7$, —$SO_3R^7$, —$SO_3M$, —$SO_2NR^7R^8$, $NR^7R^8$, $N{=}CR^7R^8$, $NH_2$, where $R^1$ to $R^6$ are identical or different;

$R^7$ and $R^8$ are each hydrogen, a substituted or unsubstituted, aliphatic or aromatic hydrocarbon radical having from 1 to 25 carbon atoms, and may be identical or different;

M is an alkali metal, alkaline earth metal, ammonium or phosphonium ion;

Q is a substituted or unsubstituted divalent aliphatic, alicyclic, aliphatic-alicyclic, aromatic, aliphatic-aromatic hydrocarbon or heterocyclic or aliphatic heterocyclic radical having from 1 to 50 carbon atoms, and in open-chain structural elements, one or more methylene groups may be replaced by oxygen and/or sulfur and/or $NR^1$ and/or NH and/or one or more CH groups may be replaced by nitrogen, and W and X are each a substituted or unsubstituted aliphatic, alicyclic, aliphatic-alicyclic, aromatic, aromatic—aromatic, aliphatic-aromatic hydrocarbon, heterocyclic or aliphatic heterocyclic radical having from 1 to 50 carbon atoms which may be identical or different or covalently linked to one another, where the substituents are selected from the group consisting of an aliphatic, alicyclic, aliphatic-alicyclic, aromatic, aromatic—aromatic, aliphatic-aromatic hydrocarbon heterocyclic or aliphatic-heterocyclic radical having 1 to 50 carbon atoms, F, Cl, Br, I, —$CF_3$, —$OR^{25}$, —$COR^{25}$, —$CO_2R^{25}$, —$CO_2M$, —$SR^{25}$, —SO$_2$R$^{25}$, —SOR$^{25}$, —SO$_3$R$^{25}$, —SO$_3$M, —SO$_2$NR$^{25}$R$^{26}$, NR$^{25}$R$^{26}$, N=CR$^{25}$R$^{26}$, NH$_2$, provided that when the phosphite oxygens linked to W and X are each linked to an aromatic ring then they are not linked to the same aromatic ring.

6. A bisphosphite as claimed in claim 5, wherein W and X are each an aliphatic, alicyclic, aliphatic-alicyclic, aromatic, aromatic—aromatic, aliphatic-aromatic hydrocarbon, heterocyclic, or aromatic-heterocyclic radical having from 1 to 50 carbon atoms which are covalently linked to form, with the attached

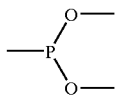

group, the structure

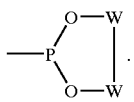

7. A bisphosphite as claimed in claim 5, wherein W and X are each substituted or unsubstituted aromatic hydrocarbon radicals having, from 1 to 50 carbon atoms which are covalently linked to form, with the attached

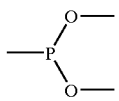

group, the structure

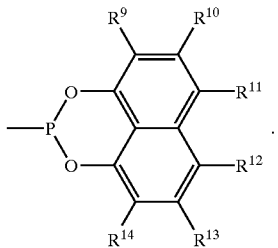

wherein R$^9$, R$^{10}$, R$^{11}$, R$^{12}$, R$^{13}$, and R$^{14}$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —CF$_3$, —OR$^{25}$, —COR$^{25}$, —CO$_2$R$^{25}$, —CO$_2$M, —SR$^{25}$, —SO$_2$R$^{25}$, —SOR$^{25}$, —SO$_3$R$^{25}$, —SO$_3$M, —SO$_2$NR$^{25}$R$^{26}$, NR$^{25}$R$^{26}$, N=CR$^{25}$R$^{26}$, NH$_2$, where R$^9$ to R$^{14}$ are identical or different and may be covalently linked to one another, R$^{25}$ and R$^{26}$ are each hydrogen or a substituted or unsubstituted, aliphatic or aromatic hydrocarbon radical having from 1 to 25 carbon atoms, and may be identical or different, and M is an alkali metal, alkaline earth metal, am phosphonium ion.

8. A bisphosphite as claimed in claim 5, wherein W and X are each substituted or unsubstituted aromatic hydrocarbon radicals having from 1 to 50 carbon atoms which are covalently linked, with the attached

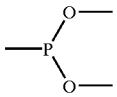

to form the structure

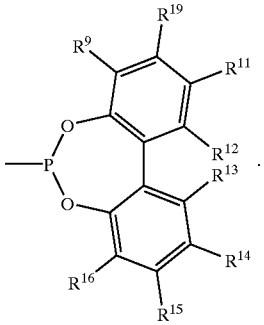

where R$^9$, R$^{10}$, R$^{11}$, R$^{12}$, R$^{13}$, R$^{14}$, R$^{15}$ and R$^{16}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —CF$_3$, —OR$^{25}$, —COR$^{25}$, —CO$_2$R$^{25}$, —CO$_2$M, —SR$^{25}$, —SO$_2$R$^{25}$, —SOR$^{25}$, —SO$_3$R$^{25}$, —SO$_3$M, —SO$_2$NR$^{25}$R$^{26}$, NR$^{25}$R$^{26}$, N=CR$^{25}$R$^{26}$, NH$_2$, where R$^9$ to R$^{16}$ are identical or different and may be covalently linked to one another, R$^{25}$ and R$^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

9. A bisphosphite as claimed in claim 1, wherein Q is a radical of the formula VIII (VIII)

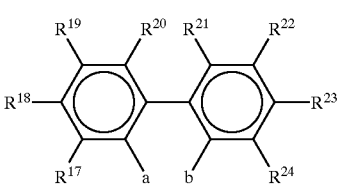

where R$^{17}$, R$^{18}$, R$^{19}$, R$^{20}$, R$^{21}$, R$^{22}$, R$^{23}$ and R$^{24}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —CF$_3$, —OR$^{25}$, —COR$^{25}$, —CO$_2$R$^{25}$, —CO$_2$M, —SR$^{25}$, —SO$_2$R$^{25}$, —SOR$^{25}$, —SO$_3$R$^{25}$, —SO$_3$M, —SO$_2$NR$^{25}$R$^{26}$, NR$^{25}$R$^{26}$, N=CR$^{25}$R$^{26}$, NH$_2$, where R$^{17}$ to R$^{24}$ are identical or different and may be covalently linked to one another, R$^{25}$ and R$^{26}$ are each hydrogen or a substituted or unsubstituted, aliphatic or aromatic hydrocarbon radical having from 1 to 25 carbon atoms, M is an alkali metal, alkaline earth metal, ammonium or phosphonium ion, and positions a and b are linkage points.

10. A bisphosphite-metal complex comprising a metal of transition Group 4, 5, 6, 7 or 8 of the Periodic Table of the Elements and one or more bisphosphites of the formula I

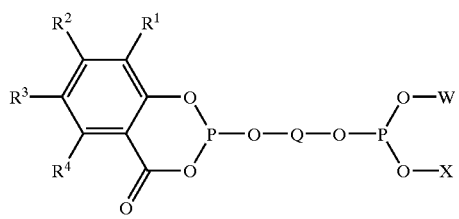
(I)

wherein $R^1$, $R^2$, $R^3$, and $R^4$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^7$, —$COR^7$, —$CO_2R^7$, —$CO_2M$, —$SR^7$, —$SO_2R^7$, —$SOR^7$, —$SO_3R^7$, —$SO_3M$, —$SO_2NR^7R^8$, $NR^7R^8$, $N=CR^7R^8$, $NH_2$, where $R^1$ to $R^4$ are identical or different and may be covalently linked to one another, $R^7$ and $R^8$ are each hydrogen, a substituted or unsubstituted, aliphatic or aromatic hydrocarbon radical having from 1 to 25 carbon atoms, and may be identical or different, M is an alkali metal, alkaline earth metal, ammonium or phosphonium ion, Q is a substituted or unsubstituted divalent aliphatic, alicyclic, aliphatic-alicyclic, aromatic, aliphatic-aromatic hydrocarbon, heterocyclic or aliphatic-heterocyclic radical having from 1 to 50 carbon atoms, and in open-chain structural elements, one or more methylene groups may be replaced by oxygen and/or sulfur and/or $NR^1$ and/or NH and/or one or more CH groups may be replaced by nitrogen, and W and X are each a substituted or unsubstituted aliphatic, alicyclic, aliphatic-alicyclic, aromatic, aliphatic-aromatic hydrocarbon, heterocyclic or aliphatic-heterocyclic radical having from 1 to 50 carbon atoms which may be identical or different or covalently linked to one another, where the substituents are selected from the group consisting of an aliphatic, alicyclic, aliphatic-alicyclic, aromatic, aromatic—aromatic, aliphatic-aromatic hydrocarbon heterocyclic or aliphatic-heterocyclic radical having 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, provided that when the phosphite oxygens linked to W and X are each linked to an aromatic ring then they are not linked to the same aromatic ring.

11. A bisphosphite-metal complex comprising a metal of transition Group 4, 5, 6, 7 or 8 of the Periodic Table of the Elements and one or more bisphosphites of the formulae II, III and/or IV

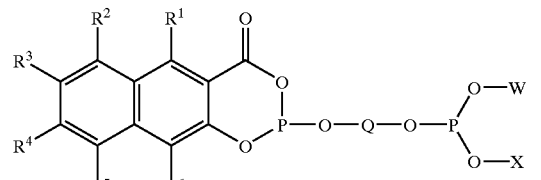
(II)

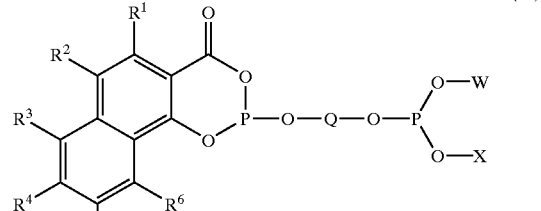
(III)

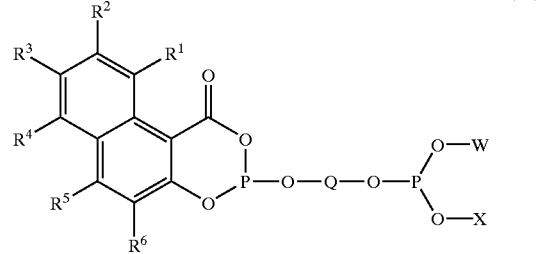
(IV)

wherein $R^1$, $R^2$, $R^3$, $R^4$, $R^5$ and $R^6$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^7$, —$COR^7$, —$CO_2R^7$, —$CO_2M$, —$SR^7$, —$SO_2R^7$, —$SOR^7$, —$SO_3R^7$, —$SO_3M$, $SO_2NR^7R^8$, $NR^7R^8$, $N=CR^7R^8$, $NH_2$, where $R^1$ to $R^6$ are identical or different, $R^7$ and $R^8$ are each hydrogen, a substituted or unsubstituted, aliphatic or aromatic hydrocarbon radical having from 1 to 25 carbon atoms, and may be identical or different, M is an alkali metal, alkaline earth metal, ammonium or phosphonium ion, Q is a substituted or unsubstituted divalent aliphatic, alicyclic, aliphatic-alicyclic, aromatic, aromatic—aromatic, aliphatic-aromatic hydrocarbon or heterocyclic or aliphatic-heterocyclic radical having from 1 to 50 carbon atoms, and in open-chain structural elements, one or more methylene groups may be replaced by oxygen and/or sulfur and/or $NR^1$ and/or NH and/or one or more CH groups may be replaced by nitrogen, and W and X are each a substituted or unsubstituted aliphatic, alicyclic, aliphatic-alicyclic, aromatic, aromatic—aromatic, aliphatic-aromatic hydrocarbon or heterocyclic or aliphatic-heterocyclic radical having from 1 to 50 carbon atoms which may be identical or different or covalently linked to one another, where the substituents are selected from the group consisting of an aliphatic, alicyclic, aliphatic-alicyclic, aromatic, aromatic—aromatic, aliphatic-aromatic hydrocarbon, heterocyclic or aliphatic-heterocyclic radical having 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, provided that when the phosphite oxygens linked to W and X are each linked to an aromatic ring then they are not linked to the same aromatic ring.

12. A bisphosphite-metal complex as claimed in claim 10, wherein W and X are aliphatic, alicyclic, aliphatic-alicyclic, aromatic, aromatic—aromatic, aliphatic-aromatic hydrocarbon, heterocyclic or aliphatic-heterocyclic radicals having from 1 to 50 carbon atoms which are covalently linked as shown in formula V

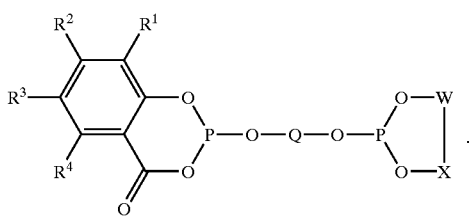

(V)

13. A bisphosphite-metal complex as claimed in claim 10, wherein W and X are each a substituted or unsubstituted aromatic hydrocarbon radical having from 1 to 50 carbon atoms which is covalently linked as shown in formula VI

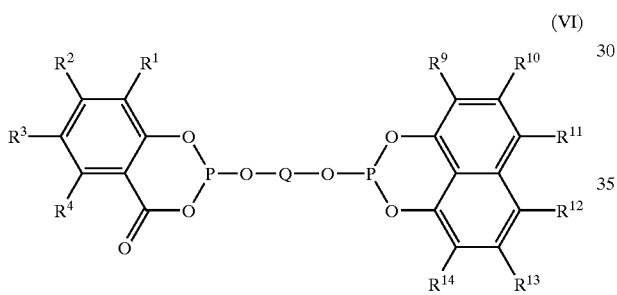

(VI)

wherein $R^9$, $R^{10}$, $R^{11}$, $R^{12}$, $R^{13}$, and $R^{14}$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, where $R^9$ to $R^{14}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

14. A bisphosphite-metal complex as claimed in claim 10, wherein W and X are each a substituted or unsubstituted aromatic hydrocarbon radical having from 1 to 50 carbon atoms which are covalently linked as shown in formula VII

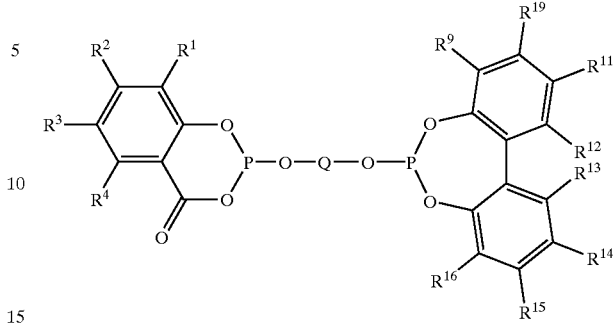

(VII)

wherein $R^9$, $R^{10}$, $R^{11}$, $R^{12}$, $R^{13}$, $R^{14}$, $R^{15}$ and $R^{16}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, where $R^9$ to $R^{16}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

15. A bisphosphite-metal complex as claimed in claim 11, wherein W and X are aliphatic, alicyclic, aliphatic-alicyclic, aromatic, aromatic—aromatic, aliphatic-aromatic hydrocarbon, heterocyclic or aliphatic-heterocyclic radicals having from 1 to 50 carbon atoms which are covalently linked to form, with the attached

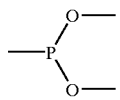

group, the structure

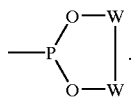

16. A bisphosphite-metal complex as claimed in claim 11, wherein W and X are each a substituted or unsubstituted aromatic hydrocarbon radical having from 1 to 50 carbon atoms which is covalently linked to form, with the attached

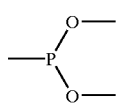

group, the structure

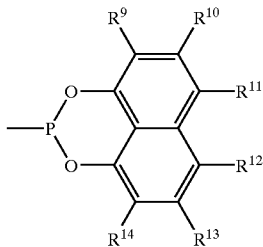

wherein $R^9$, $R^{10}$, $R^{11}$, $R^{12}$, $R^{13}$, and $R^{14}$ are each hydrogen, an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$,
—$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, where $R^9$ to $R^{14}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

17. A bisphosphite-metal complex as claimed in claim 11, wherein W and X are each a substituted or unsubstituted aromatic hydrocarbon radical having from 1 to 50 carbon atoms which are covalently linked to form with the attached

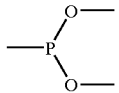

group, the structure

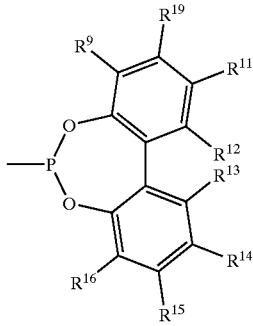

wherein $R^9$, $R^{10}$, $R^{11}$, $R^{12}$, $R^{13}$, $R^{14}$, $R^{15}$ and $R^{16}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$,
—$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, where $R^9$ to $R^{16}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, and may be identical or different, and M is an alkali metal, alkaline earth metal, ammonium or phosphonium ion.

18. A bisphosphite-metal complex as claimed in claim 10, wherein Q is a hydrocarbon radical of the formula VIII

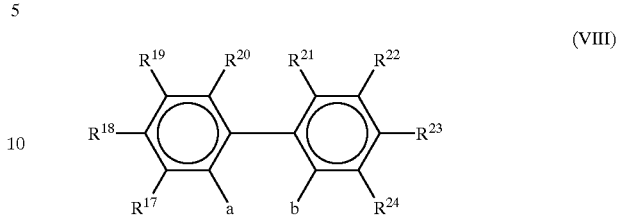

(VIII)

where $R^{17}$, $R^{18}$, $R^{19}$, $R^{20}$, $R^{21}$, $R^{22}$, $R^{23}$ and $R^{24}$ are each hydrogen or an aliphatic, alicyclic, aliphatic-alicyclic, aromatic, aromatic—aromatic, aliphatic-aromatic hydrocarbon, heterocyclic or aliphatic-heterocyclic radical having from 1 to 50 carbon atoms, F, Cl, Br, I, —$CF_3$, —$OR^{25}$, —$COR^{25}$, —$CO_2R^{25}$, —$CO_2M$, —$SR^{25}$, —$SO_2R^{25}$, —$SOR^{25}$, —$SO_3R^{25}$, —$SO_3M$, —$SO_2NR^{25}R^{26}$, $NR^{25}R^{26}$, $N=CR^{25}R^{26}$, $NH_2$, where $R^{17}$ to $R^{24}$ are identical or different and may be covalently linked to one another, $R^{25}$ and $R^{26}$ are each hydrogen or a substituted or unsubstituted, aliphatic or aromatic hydrocarbon radical having from 1 to 25 carbon atoms, M is an alkali metal, alkaline earth metal, ammonium or phosphonium ion, and positions a and b are linkage points.

19. A bisphosphite-metal complex as claimed in claim 10, wherein the metal is rhodium, platinum, cobalt or ruthenium.

20. A method for the hydroformylation of olefins, comprising:

hydroformylating an olefin reactant under hydroformylation conditions in the presence of a bisphosphite-metal complex as claimed in claim 10.

21. A method for the hydroformylation of olefins, comprising:

hydroformylating an olefin reactant under hydroformylation conditions in the presence of a bisphosphite-metal complex formed from a combination of the bisphosphite of formula (I) in claim 10 and another metal complexing phosphorus ligand.

22. The method according to claim 20, wherein the olefin reactant is propene, 1-butene, cis-2-butene, trans-2-butene, isobutene, butadiene, mixtures of $C_4$-olefins, 1- or 2-pentene, 2-methyl-1-butene, 2-methyl-2-butene, 3-methyl-1-butene, 1-, 2- or 3-hexene, the $C_6$-olefin mixtures formed in the dimerization of propene (dipropene), 1-heptene, heptenes, 2-or 3-methyl-1-hexene, 1-octene, octenes, 2-methylheptenes, 3-methylheptenes, 5-methyl 2-heptene, 6-methyl-2-heptene, 2-ethyl-1-hexene, the isomeric $C_8$-olefin mixtures formed in the dimerization of butenes (dibutene), 1-nonene, nonenes, 2- or 3-methyloctenes, the $C_9$-olefin mixtures formed in the trimerization of propene (tripropene), decenes, 2-ethyl 1-octene, dodecenes, the $C_{12}$-olefin mixture formed in the tetramerization of propene or the trimerization of butenes (tetrapropene or tributene), tetradecene, hexadecenes, the $C_{16}$-olefin mixtures formed in the tetramerization of butenes (tetrabutene) and olefin mixtures prepared by co-oligomerization of olefins having different numbers of carbon atoms.

* * * * *